(12) United States Patent
Oh et al.

(10) Patent No.: US 11,825,926 B2
(45) Date of Patent: Nov. 28, 2023

(54) ADHESIVE GEL NAIL AND MANUFACTURING METHOD THEREOF

(71) Applicant: Naeil Teem Co., Ltd., Seoul (KR)

(72) Inventors: Min Woo Oh, Incheon (KR); Seong Ju Han, Gyeonggi-do (KR)

(73) Assignee: Naeil Teem Co., Ltd., Seoul (KR)

( * ) Notice: Subject to any disclaimer, the term of this patent is extended or adjusted under 35 U.S.C. 154(b) by 213 days.

(21) Appl. No.: 17/404,683

(22) Filed: Aug. 17, 2021

(65) Prior Publication Data
US 2022/0053908 A1 Feb. 24, 2022

(30) Foreign Application Priority Data
Aug. 18, 2020 (KR) .......................... 10-2020-0103448

(51) Int. Cl.
| | |
|---|---|
| *A61Q 3/02* | (2006.01) |
| *A61Q 3/00* | (2006.01) |
| *C09D 4/00* | (2006.01) |
| *A45D 31/00* | (2006.01) |
| *A61K 8/9789* | (2017.01) |
| *A61K 8/19* | (2006.01) |
| *A61K 8/67* | (2006.01) |
| *A61K 8/73* | (2006.01) |
| *A61Q 17/00* | (2006.01) |
| *B05D 7/00* | (2006.01) |

(52) U.S. Cl.
CPC ................ *A45D 31/00* (2013.01); *A61K 8/19* (2013.01); *A61K 8/673* (2013.01); *A61K 8/678* (2013.01); *A61K 8/731* (2013.01); *A61K 8/9789* (2017.08); *A61Q 3/02* (2013.01); *A61Q 17/005* (2013.01); *B05D 7/58* (2013.01)

(58) Field of Classification Search
CPC . A61Q 3/02; A61Q 3/00; A61K 8/042; A61K 2800/81; A61K 8/87; A61K 2800/884; A61K 2800/42; A61K 8/0241
See application file for complete search history.

(56) References Cited

U.S. PATENT DOCUMENTS

| | | | |
|---|---|---|---|
| 10,376,024 B2 | 8/2019 | Yu et al. | |
| 2010/0178262 A1* | 7/2010 | Kergosien | ............... A61K 8/361 424/61 |
| 2014/0251360 A1 | 9/2014 | Kim et al. | |
| 2017/0312207 A1* | 11/2017 | Saeki | ........................ A61K 8/73 |
| 2018/0168295 A1* | 6/2018 | Yu | ........................... B32B 27/08 |

(Continued)

FOREIGN PATENT DOCUMENTS

| | | | |
|---|---|---|---|
| CN | 102920637 A | * | 2/2013 |
| JP | 4324241 B1 | * | 9/2009 |
| JP | 2011072325 A | * | 4/2011 |

(Continued)

*Primary Examiner* — Tracy Liu
(74) *Attorney, Agent, or Firm* — Renner, Otto, Boisselle & Sklar (57) ABSTRACT

Provided is an adhesive gel nail which includes a base film, an adhesive layer on the base film, a printed layer on the adhesive layer, an UV gel coating layer on the printed layer, an LED gel coating layer on the UV gel coating layer, and a highpoint glossy-top coating layer on the LED gel coating layer, and the highpoint glossy-top coating layer is formed by applying and drying a glossy-top coating solution in which a monomer, an oligomer, a cellulose, and a long-wavelength initiator are mixed.

14 Claims, 6 Drawing Sheets

(56) References Cited

U.S. PATENT DOCUMENTS

2018/0352933 A1  12/2018  Azuma
2019/0328090 A1  10/2019  Yu et al.

FOREIGN PATENT DOCUMENTS

| | | | | |
|---|---|---|---|---|
| JP | 2016-175883 | A | | 10/2016 |
| JP | 2016175883 | A | * | 10/2016 |
| JP | 2017-123972 | A | | 7/2017 |
| KR | 10-20113-0103452 | A | | 9/2013 |
| KR | 10-1342492 | B | | 12/2013 |
| KR | 10-2014-0105144 | A | | 9/2014 |
| KR | 20140105144 | A | * | 9/2014 |
| KR | 10-1797203 | B | | 11/2017 |
| KR | 10-1882174 | B | | 7/2018 |
| KR | 10-2018-0092475 | A | | 8/2018 |
| KR | 10-2019-0014044 | A | | 2/2019 |
| KR | 10-2019-0017832 | A | | 2/2019 |
| KR | 10-2019-0017833 | A | | 2/2019 |
| KR | 20190017832 | A | * | 2/2019 |
| KR | 10-2024663 | B | | 9/2019 |
| KR | 10-2024666 | B | | 9/2019 |
| KR | 10-2020-0104095 | A | | 9/2020 |
| WO | WO-2014028020 | A1 | * | 2/2014 ............... A61K 8/34 |

* cited by examiner

ADHESIVE GEL NAIL AND MANUFACTURING METHOD THEREOF

CROSS-REFERENCE TO RELATED APPLICATION

This application claims the benefit of priority to Korean Patent Application No. 10-2020-0103448, filed in the Korean Intellectual Property Office on Aug. 18, 2020, the entire contents of which are incorporated herein by reference.

TECHNICAL FIELD

The present disclosure relates to an adhesive gel nail attachable to a nail of a user and a manufacturing method thereof.

BACKGROUND

In general, a way to apply pigments, such as various colors of manicures (or nail polish), to fingernails or toenails or a way to attach accessories, such as beads and jewels, to the fingernails has been used for the nail art.

However, the way to apply a liquid pigment to fingernails or toenails may cause inconvenience to the user because it takes a lot of time to cure the pigment after the pigment is applied thereto. In addition, even in the case of the way to attach the accessories, it takes a time until the adhesive is completely hardened; even after the attachment is completed, the accessories easily come off even by small impact.

To solve the above issues, a way to attach a nail sticker is being used instead of the way to directly apply the pigment to the fingernails or toenails of the user. According to this way, the user may decorate his/her fingernails and toenails by simply attaching stickers to his/her fingernails or toenails without waiting until the pigments are cured after applied, and thus, the user may carry out the nail art much more quickly and easily compared to conventional ways.

However, even in the case of the nail sticker, when the nail sticker is attached and detached too often, the fingernails and toenails may be damaged, thereby causing various issues such as the infiltration of foreign substances (e.g., bacteria) into the fingernails and toenails. In addition, in the case where the nail sticker is attached to the fingernail or toenail for a long time, oxygen may not be supplied for a long time. In this case, the user may feel stuffy, and an adverse influence on the health of fingernails and toenails may occur.

SUMMARY

The present disclosure has been made to solve the above-mentioned problems occurring in the prior art while advantages achieved by the prior art are maintained intact.

An aspect of the present disclosure provides an adhesive gel nail and a manufacturing method thereof, which are capable of protecting the health of fingernails and toenails through nutritional and antibacterial components included in the adhesive gel nail, providing the volume of user's fingernails and toenails through a highpoint glossy-top coating layer, and improving oxygen permeability, that is, air permeability through air holes formed within the adhesive gel nail.

The technical problems to be solved by the present disclosure are not limited to the aforementioned problems, and any other technical problems not mentioned herein will be clearly understood from the following description by those skilled in the art to which the present disclosure pertains.

According to an aspect of the present disclosure, an adhesive gel nail may include a base film, an adhesive layer on the base film, a printed layer on the adhesive layer, an UV gel coating layer on the printed layer, an LED gel coating layer on the UV gel coating layer, and a highpoint glossy-top coating layer on the LED gel coating layer, and the highpoint glossy-top coating layer may be formed by applying and drying a glossy-top coating solution in which a monomer, an oligomer, a cellulose, and a long-wavelength initiator are mixed.

According to an aspect of the present disclosure, a method of manufacturing an adhesive gel nail may include forming an adhesive layer on a base film, forming a printed layer on the adhesive layer, forming an UV gel coating layer on the printed layer, forming an LED gel coating layer on the UV gel coating layer, and forming a highpoint glossy-top coating layer on the LED gel coating layer, and the forming of the highpoint glossy-top coating layer may include forming the highpoint glossy-top coating layer by applying and drying a glossy-top coating solution in which a monomer, an oligomer, a cellulose, and a long-wavelength initiator are mixed.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Below, various embodiments of the present disclosure will be described in detail with reference to accompanying drawings. In the specification, the same reference numerals are used for the same components in drawings, and thus, additional description will be omitted to avoid redundancy.

With regard to various embodiments of the present disclosure described in the specification, specific structural and functional descriptions are for the purpose of describing an embodiment of the present disclosure, and various embodiments of the present disclosure may be carried out in various forms and should not be construed as limited to embodiments described in the specification.

The terms "first", "second", etc. used in various embodiments may modify various components regardless of an order and/or an importance, without limitation to the components. For example, without departing the scope and spirit of the invention, a first component may be referred to as a second component, and similarly, a second component may be referred to as a first component.

The terms used in the specification are only used to describe a specific embodiment and are not intended to limit the scope and spirit of the invention. The terms of a singular form may include plural forms unless otherwise specified.

Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal meaning unless expressly defined in the specification. In some cases, even in the case of terms defined in the specification, they may not be interpreted to exclude embodiments of the present disclosure.

Figure 1:
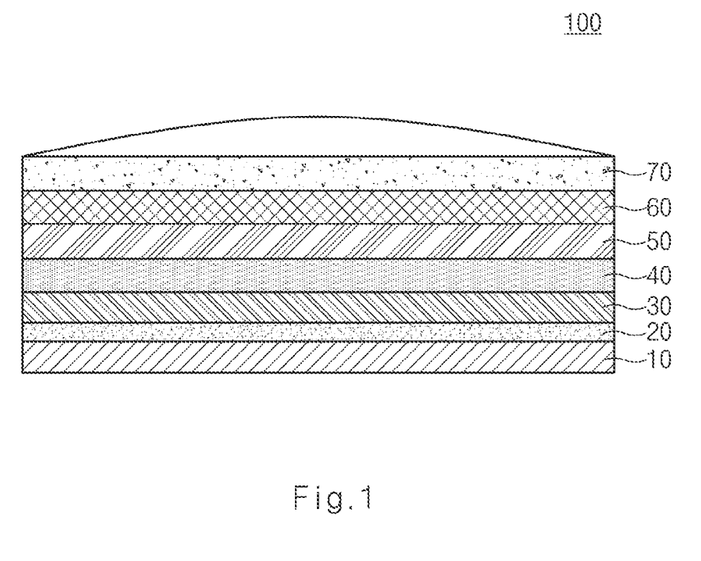
FIG. 1 is a diagram illustrating a structure of an adhesive gel nail, according to an embodiment of the present disclosure.

FIG. 1 is a diagram illustrating a structure of an adhesive gel nail, according to an embodiment of the present disclosure.

Referring to FIG. 1, an adhesive gel nail 100 according to an embodiment of the present disclosure may include a base film 10, an adhesive layer 20 provided on the base film 10, an urethane sheet layer 30 provided on the adhesive layer 20, a printed layer 40 provided on the urethane sheet layer 30, an UV gel coating layer 50 provided on the printed layer 40, an LED gel coating layer 60 provided on the UV gel coating layer 50, and a highpoint glossy-top coating layer 70 provided on the LED gel coating layer 60.

The base film 10 may be located at the lowest end of the adhesive gel nail 100 according to an embodiment of the present disclosure. For example, the base film 10 may include a silicon release-treated fabric being a 125 micron PET film.

The adhesive layer 20 may be applied on the base film 10 and may include a nutritional enhancement component for caring for fingernails and toenails as an anti-fungal nutrient glue layer and an antibacterial component for protecting fingernails from bacteria and mold. For example, the nutritional enhancement component of the adhesive layer 20 may include vitamin B5, vitamin E, calcium, and the like, and the antibacterial component thereof may include eucalyptus, cypress water, natural herb, and the like. In addition, the adhesive layer 20 may include an acrylic water-based adhesive. Through the components included in the adhesive layer 20, it may be possible to prevent the fingernails and toenails of the user from being damaged by frequent self-nail procedures and to minimize a damage of surfaces of the fingernails. For example, the adhesive layer 20 may be 20 microns in thickness.

The urethane sheet layer 30 may be applied on the adhesive layer 20 and may be formed by adding aerosol to an urethane raw material such that air holes are formed. This may allow the adhesive gel nail 100 to have high oxygen permeability, that is, the adhesive gel nail 100 may provide air permeability. Accordingly, when attaching the gel nail 100 to his/her fingernails or toenails, the user may feel more comfortable, that is, may not feel stuffy. For example, the urethane sheet layer 30 may be 40 microns in thickness.

The printed layer 40 may be applied on the urethane sheet layer 30 and may express a design of the adhesive gel nail 100 by using various printing methods or through decoration of gold leaf, silver leaf, hologram leaf, glitter, or the like. In this case, the printed layer 40 may be formed by a silk screen printing, flexographic printing, offset printing, digital printing, or gravure printing manner.

For example, the printed layer 40 may be formed by printing a color ink with a given thickness. The color ink used for the printed layer 40 may be implemented by a CMYK model, in which "C" is cyan, "M" is magenta, "Y" is yellow, and "K" is black, and the printed layer 40 may be formed by using color inks independently or through an appropriate combination thereof. In detail, a white ink layer (not illustrated) may be formed on the adhesive layer 20 that is applied on the base film 10, and the printed layer 40 may be formed on the white ink layer. As described above, to express a desired color of the adhesive gel nail 100 according to an embodiment of the present disclosure, a color ink that is obtained by combining CMYK colors or combining other colors may be applied on the white ink layer. That is, the printed layer 40 may be formed on the white ink layer such that a color of the printed layer 40 stands out very vividly.

Also, the printed layer 40 may be formed by performing coating (e.g., screen printing coating) with respect to a raw material for preventing the gel nail 100 from being quickly hardened due to external ultraviolet light or indirect ultraviolet light of a fluorescent lamp or an LED lamp. Here, a photostabilizer (e.g., TINUVIN) may be added to a raw material used for the printed layer 40 as much as 5% or less, and thus, the gel nail 100 may be prevented from being quickly hardened when exposed to indirect ultraviolet light of a fluorescent lamp or an LED lamp. Meanwhile, the printed layer 40 may be in the shape of a fingernail or a toenail. For example, the printed layer 40 may be 20 microns in thickness.

The UV gel coating layer 50 may be applied on the printed layer 40, and may be formed by applying an UV gel coating solution, in which an oligomer, a monomer, and a short-wavelength initiator are mixed, and drying the UV gel coating solution in an ultraviolet curing manner. The UV gel coating layer 50 may be formed by using an UV gel coating solution in which 40% to 60% of an oligomer, 30% to 55% of a monomer, and 2% to 10% of a short-wavelength initiator are mixed. In this case, the oligomer may use urethane, acryl, acrylic epoxy, polyester-based oligomer, or the like, and the short-wavelength initiator may use TPO, 184, or the like. In addition, the applied UV gel coating solution may be dried in an UV curing manner to form the UV gel coating layer 50. For example, the UV gel coating layer 50 may be 40 microns in thickness.

In the case of the UV gel coating layer 50, when the amount of oligomer is a reference value or more (i.e., the content of the oligomer exceeds 60%), the gel nail 100 may become very soft, thereby causing 1) deformation of the gel nail 100, and 2) a decrease of a retention characteristic due to a damage such as scratch or stabbing. Accordingly, the UV gel coating solution in which the content of the oligomer does not exceed 60% as much as possible is required.

In contrast, when the content of the oligomer is less than a reference value (i.e., the content of the oligomer is less than 40%), the gel nail 100 may become very hard, thereby making it difficult to attach the gel nail 100 to a curved fingernail of a consumer. In this case, because the adhesion decreases, the gel nail 100 may come off (i.e., the gel nail 100 may come off from a fingernail or toenail); because there is no adhesion, deformation may occur. Accordingly, it is desirable to use the UV gel coating solution in which the content of the oligomer is 40% or more.

Meanwhile, when the content of the monomer exceeds a reference value (e.g., 55% in content) in the UV gel coating layer 50, the flexibility and elongation of the product may decrease, and the adhesion to the curved fingernail or toenail may decrease. This may means that a sustaining characteristic is reduced. In contrast, when the content of the monomer is less than a reference value (e.g., 30%), the gel nail 100 may become very hard, thereby causing a decrease of the adhesion when attached to a curved fingernail, that is, a decrease of the sustaining characteristic (i.e., the adhesion to a fingernail or toenail). For this reason, it is desirable to use the UV gel coating solution in which the content of the oligomer ranges from 30% to 55%.

Here, the adhesion to the fingernail or toenail means that a lower adhesive layer (not illustrated) under the base film 10 of the gel nail 100 is in a state of being attached to a curved fingernail or toenail of the user without separation therefrom. The improvement of adhesion of the lower adhesive layer may allow the adhesion of the adhesive gel nail 100 to a fingernail or toenail to become good.

Also, when the content of the short-wavelength initiator exceeds 10% in the UV gel coating layer 50, a curing state of the product may become too fast to cause natural curing in the process of manufacturing or distributing the product, thereby making it difficult to attach the gel nail 100 to a curved fingernail or toenail of the user. Even though attached, the gel nail 100 may easily come off from the fingernail or toenail. To prevent the above issue, in the case of the UV gel coating layer 50, the short-wavelength initiator may be mixed not to exceed 10%.

In contrast, in the case where the content of the short-wavelength initiator is less than a reference value (e.g., 2%), a curing speed may decrease, thereby causing the reduction of firmness of the product. As a result, foreign substances may easily stick to fingernails or toenails, deformation may easily occur, and a retention characteristic may also decrease. Accordingly, it is desirable to adjust the content of the short-wavelength initiator used in the UV gel coating layer 50 so as to be 2% or more.

The LED gel coating layer 60 may be applied on the UV gel coating layer 50 and may be formed by applying and drying an LED gel coating solution in which an oligomer, a monomer, a long-wavelength initiator, and a cellulose are mixed. The LED gel coating layer 60 may be formed by using an UV gel coating solution in which 15% to 40% of an oligomer, 20% to 30% of a monomer, 0.1% to 0.5% of a long-wavelength initiator, and 30% to 55% of a cellulose are mixed. Also, the applied LED gel coating solution may form the LED gel coating layer 60 by drying the solution at a temperature of 60 to 100 degrees for 30 to 60 minutes. As such, the UV gel coating layer 50 and the LED gel coating layer 60 that are transparent coating layers may protect the printed layer 40. For example, the LED gel coating layer 60 may be 220 microns in thickness.

In the case of the LED gel coating layer 60, when the amount of monomer exceeds a reference value (e.g., 30%), the stickiness of the gel nail 100 may become severe, and firmness may be reduced. Also, the gel nail 100 may be gotten on the user's hand, and the shape of the gel nail 100 may be damaged. A curing speed of the product also decreases greatly. To prevent this phenomenon, it is desirable to adjust the content of the monomer to 30% or less in the LED gel coating layer 60. In contrast, when the content of the monomer is less than 20%, the gel nail 100 may become very hard, thereby causing the reduction of adhesion when attaching the gel nail 100 to a curved fingernail. This may mean that the retention characteristic is also reduced. Accordingly, it is desirable to use the LED gel coating solution in which the content of the oligomer is 20% or more.

Meanwhile, when the content of the oligomer included in the LED gel coating layer 60 exceeds 40%, the LED gel coating layer 60 may be easily cured by ultraviolet light. That is, natural curing may easily occur in the process of manufacturing or distributing the gel nail 100. For this reason, when the user removes the gel nail 100 after the LED gel coating layer 60 is cured, the LED gel coating layer 60 may not be completely removed and may peel off as it splits. In this case, a fingernail may be damaged. In contrast, when the content of the oligomer is less than 15%, a curing speed may become very slow during UV curing, so that curing fails to be completely made. In the case where an uncured product is used in this state, the gel nail 100 may be severely damaged. This may cause the deformation of the shape of the gel nail 100 and the reduction of glossiness. Also, the retention characteristic of the gel nail 100 may decrease due to foreign substances.

In addition, when the content of the long-wavelength initiator of the LED gel coating layer 60 exceeds 0.5%, natural curing may easily occur due to exposure to light in real life, thereby making it difficult to easily attach the gel nail 100 to a curved fingernail or toenail of the user. Even after attached, the gel nail 100 may easily come off. When the content of the long-wavelength initiator is less than 0.1%, a curing speed may become very slow, and the firmness of the gel nail 100 may be reduced. For this reason, foreign substances may easily adhere, deformation may easily occur, and a retention characteristic may decrease.

Also, when the content of the cellulose of the LED gel coating layer 60 exceeds 55%, the elongation of the gel nail 100 may become very low, thereby making it difficult to attach the gel nail 100 to a curved fingernail or toenail. That is, because the gel nail 100 is not completely in close contact with the user's fingernail or toenail and easily comes off, the adhesion and a retention characteristic of the gel nail 100 may decrease. Accordingly, it is desirable to mix the cellulose in the LED gel coating layer 60 so as to be 55% or less. In contrast, when the content of the cellulose as less than 30%, because a function of making the gel nail 100 in a semi-solid state degrades, it is necessary to make the content of the cellulose more than 30%.

The highpoint glossy-top coating layer 70 may be applied on the LED gel coating layer 60 and may be formed by applying and drying a glossy-top coating solution in which a monomer, an oligomer, a cellulose, and a long-wavelength initiator are mixed. In this case, the highpoint glossy-top coating layer 70 may have a shape in which a central port don thereof protrudes. Also, the highpoint glossy-top coating layer 70 may be harder than the LED gel coating layer 60. For example, the highpoint glossy-top coating layer 70 may be formed by driving a glossy-top coating solution, in which 3% to 12% of a monomer, 9% to 25% of an oligomer, 60% to 88% of a cellulose, and 0.2% to 0.7% of a long-wavelength initiator are mixed, at a temperature of 60° C. to 100° C. for 30 to 60 minutes. For example, the highpoint glossy-top coating layer 70 may be 40 microns in thickness.

The adhesive gel nail 100 according to an embodiment of the present disclosure may have a thickness between 200 and 500 microns through the process of forming the above highpoint glossy-top coating layer 70. That is, as the lowest thickness of 200 microns and the highest thickness of 500 microns are implemented from a cuticle line to the center of the fingernail or toenail so as to fit to the curvature of the fingernail or toenail, it may be possible to adjust the thickness of the gel nail 100 and to implement a high point. As such, an epoxy and emboss effect may be imparted to the gel nail 100.

As such, the process of implementing the thick feeling of the adhesive gel nail 100 may be applied to all of a silk screen engraving technology, a mechanical method using a pressure tube, and a direct squeezing method; in the case of the silk screen engraving, a thick shape may be implemented by applying thick film engraving or general engraving so as to be printed with a thickness of 200 to 500 microns.

In addition, the highpoint glossy-top coating layer 70 may further include a protective film layer (not shown) provided thereon. In this case, the protective film layer may be an easy-cutting film cover capable of being cut without a cut line. Accordingly, the user may easily make cutting, thus improving the convenience of user.

Meanwhile, the adhesive gel nail 100 according to an embodiment of the present disclosure may have a modulus value of 1 Mpa to 35 Mpa. Here, the modulus of the gel nail 100 may mean a numerical value of elasticity. This may make it possible to enhance the adhesion of the gel nail to a curved surface of a fingernail or toenail by implementing a resilient texture and to provide a fitting force so as to fit to a tip shape of the fingernail or toenail.

For example, all of the monomer, the oligomer, and the long-wavelength initiator used in the adhesive gel nail 100 according to an embodiment of the present disclosure are products in a liquid state and change from a liquid state to a solid state only when exposed to ultraviolet light. In this case, the cellulose may perform a function of making the gel nail 100 from a liquid state to a semi-solid state.

In addition, the adhesive gel nail 100 according to an embodiment of the present disclosure may be implemented by cutting the adhesive layer 20, the urethane sheet layer 30, the printed layer 40, and the UV gel coating layer 50 formed on the base film 10 by a punching process so as to have a fingernail or toenail shape. After the punching process, a process of cutting the base film 10 may be further performed to form an adhesive gel nail.

Meanwhile, a part of the layers 20 to 60 of the adhesive gel nail 100 according to an embodiment of the present disclosure shown in FIG. 1 may be omitted. Also, the order of applying the layers 20 to 60 is not limited to FIG. 1, and the layers 20 to 60 may be applied in an order different from that of FIG. 1 if necessary.

As described above, an adhesive gel nail according to an embodiment of the present disclosure may include nutritional and antibacterial components to prevent fingernails and toenails from being damaged. Also, the adhesive gel nail according to an embodiment of the present disclosure may provide a volume to the user's fingernails and toenails through a highpoint glossy-top coating layer. In addition, as air holes are formed within the adhesive gel nail such that oxygen permeability is improved, the adhesive gel nail may provide air permeability.

Figure 2:
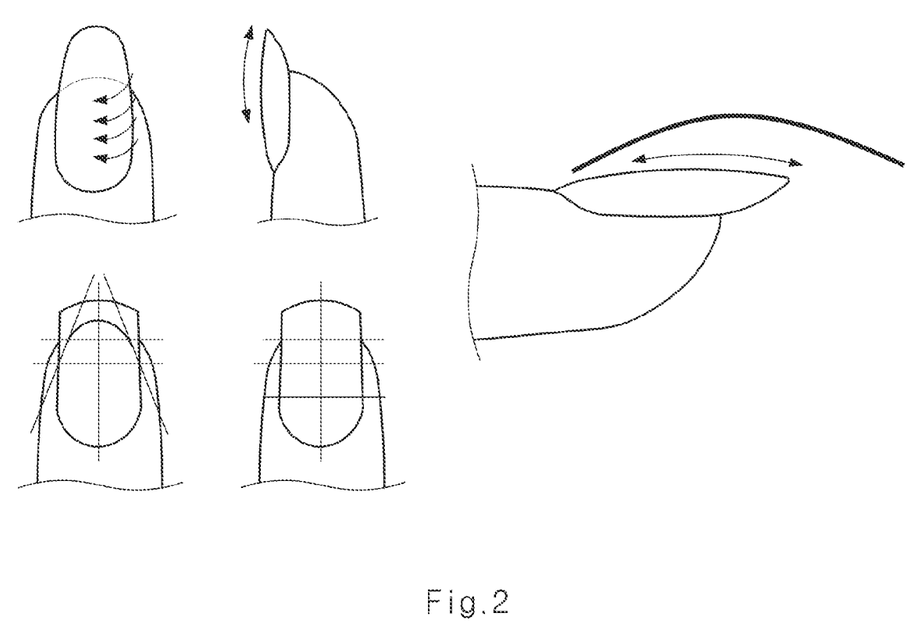
FIG. 2 is a diagram illustrating how to implement a high point through a highpoint glossy-top coating layer of an adhesive gel nail, according to an embodiment of the present disclosure.

FIG. 2 is a diagram illustrating how to implement a high point through a highpoint glossy-top coating layer of an adhesive gel nail, according to an embodiment of the present disclosure.

Referring to FIG. 2, the adhesive gel nail according to an embodiment of the present disclosure may include a high-point glossy-top coating layer at the uppermost end thereof to implement a high point shape having a thickness of 200 to 500 microns. Accordingly, the adhesive gel nail according to an embodiment of the present disclosure may have a volume compared to a conventional nail sticker and may exhibit a glossy luster.

In detail, a gel coating layer of the adhesive gel nail according to an embodiment of the present disclosure may be implemented by two application steps. In this case, a lower layer corresponding to the first application step is printed at a ratio in which the content of a monomer being a connecting component does not exceed 30% to 50%, and an upper layer corresponding to the second application step is printed at a rate in which the content of the monomer does not exceed 20% to 30%. When dried in an UV dryer after finishing the above printing work, the product may maintain a high gloss effect without stickiness, thus preventing a damage of the gel nail, such as scratches.

In addition, the monomer, the oligomer, and the long-wavelength initiator described above may generally be liquid raw materials, and a gel raw material of a semi-solid state may be formed by mixing 30% or more of the cellulose therewith. After the above process is finished, Thomson cut (i.e., a punching process or Thomson kiss-cut) may be performed to make the gel raw material thick, and after removing a sheet paper on a surface of the gel raw material, an LED gel coating layer may be printed on the upper layer corresponding to the second application step. After the LED gel coating layer is formed, the Thompson cut is performed, and the sheet paper attached to the surface thereof is removed.

In addition, a printing process for making a thick effect of the product may be performed after a punching process; in the case where a surrounding sheet paper is removed after punching, only a designed gel nail product remains. Afterwards, an LED gel coating solution may be printed with a thickness of 200 to 500 micrometers through screen printing in a state of focusing an engraved frame by using the remaining portion and silks. A resultant structure after printing may be dried in a drying apparatus at a temperature of 60 to 70 degrees for 30 to 40 minutes, and thus, a gel nail as shown in FIG. 2 may be formed.

Figure 3A:
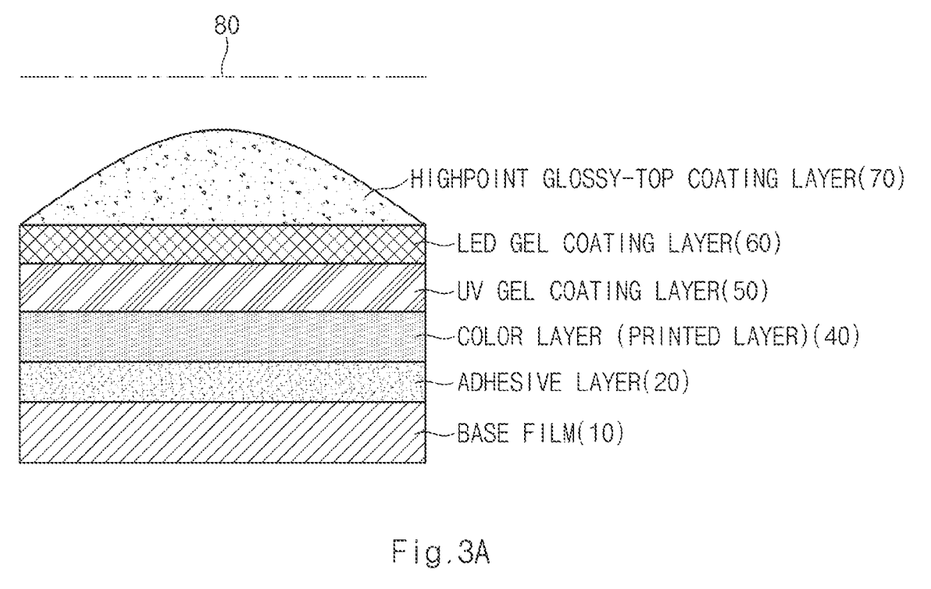
FIG. 3A is a diagram illustrating a protective film layer of an adhesive gel nail, according to an embodiment of the present disclosure.
Figure 3B:
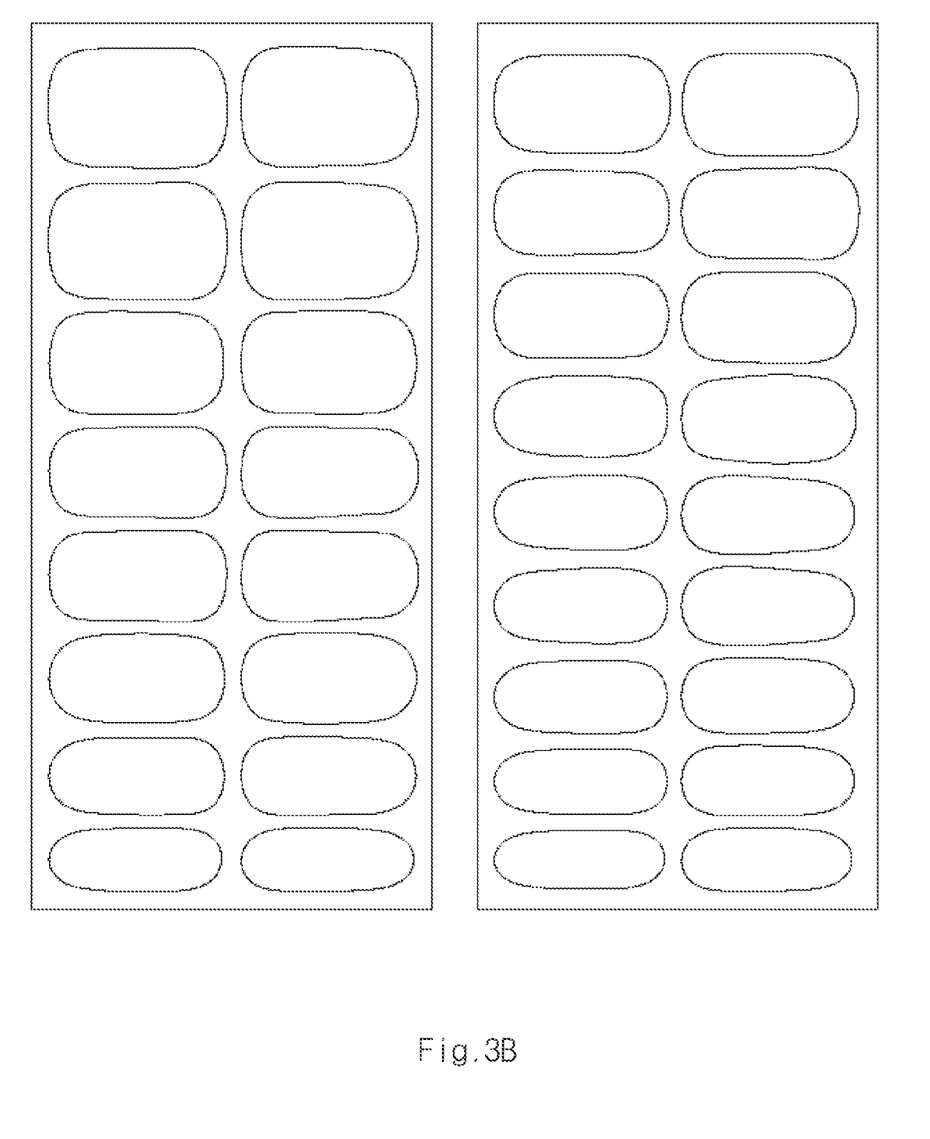
FIGS. 3B and 3C are diagrams illustrating examples of adhesive gel nails for fingernail and toenail including a protective film layer.
Figure 3C:
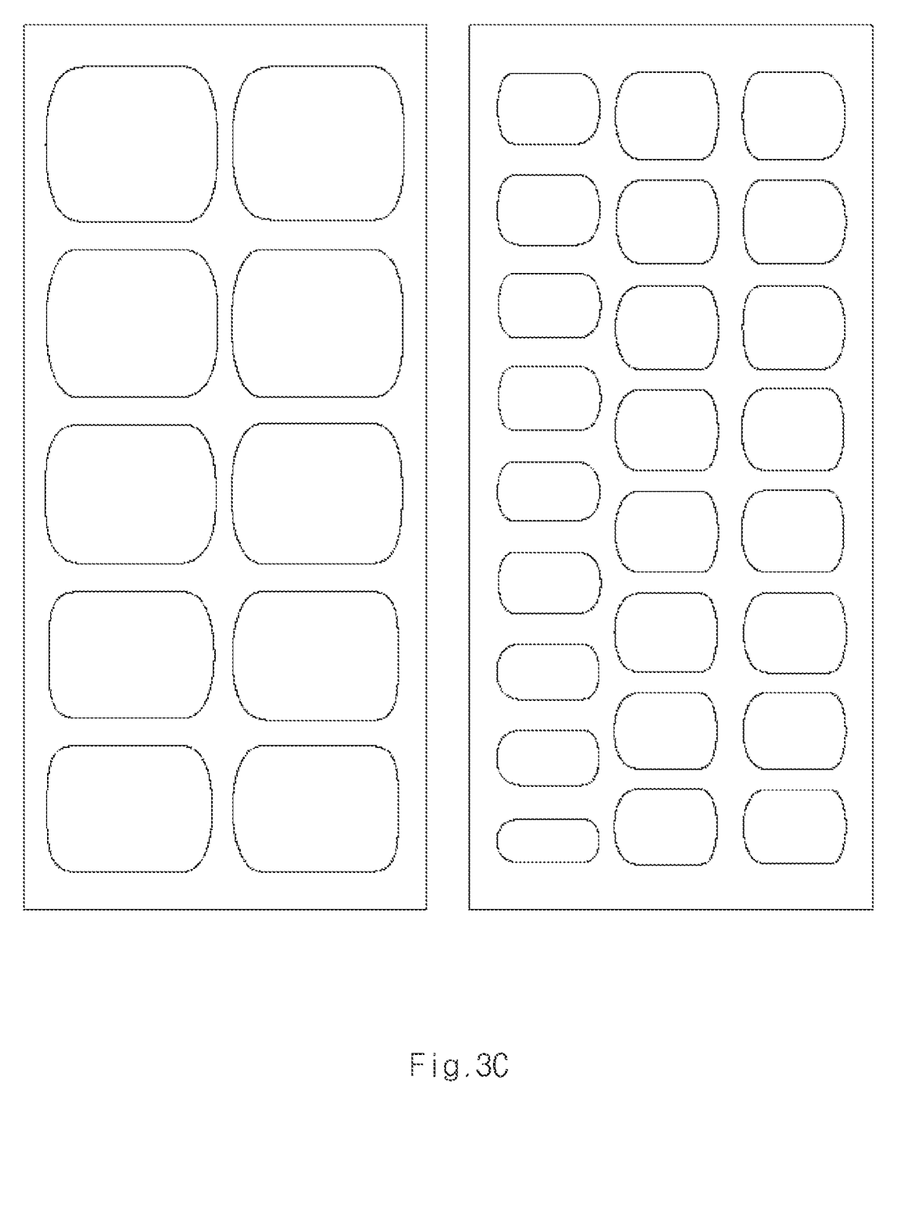

FIG. 3A is a diagram illustrating a protective film layer of an adhesive gel nail, according to an embodiment of the present disclosure, and FIGS. 3B and 3C are diagrams showing examples of adhesive gel nails for fingernail and toenail including a protective film layer.

As illustrated in FIG. 3A, the adhesive gel nail according to an embodiment of the present disclosure may include a protective film layer 80 on the highpoint glossy-top coating layer 70. In this case, the protective film layer 80 may protect the highpoint glossy-top coating layer 70 from external impact.

In addition, as an easy-cutting manner is applied to the protective film layer 80, even without a cut line, the protective film layer 80 may allow the user to easily cut the gel nail required for use. For example, as illustrated in FIGS. 3B and 3C, as the protective film layer 80 is included in various types of gel nails for fingernail or toenail, the user may conveniently attach and detach each gel nail.

As such, the adhesive gel nail according to an embodiment of the present disclosure may allow the user to simply and easily conduct cutting through the protective film layer 80 and to use the gel nail and at the same time, may protect a highpoint glossy-top coating layer from external pollutants or scratches. However, the adhesive gel nail according to an embodiment of the present disclosure does not necessarily include the protective film layer 80 on the highpoint glossy-top coating layer 70, and the protective film layer 80 may be omitted if necessary.

Figure 4:
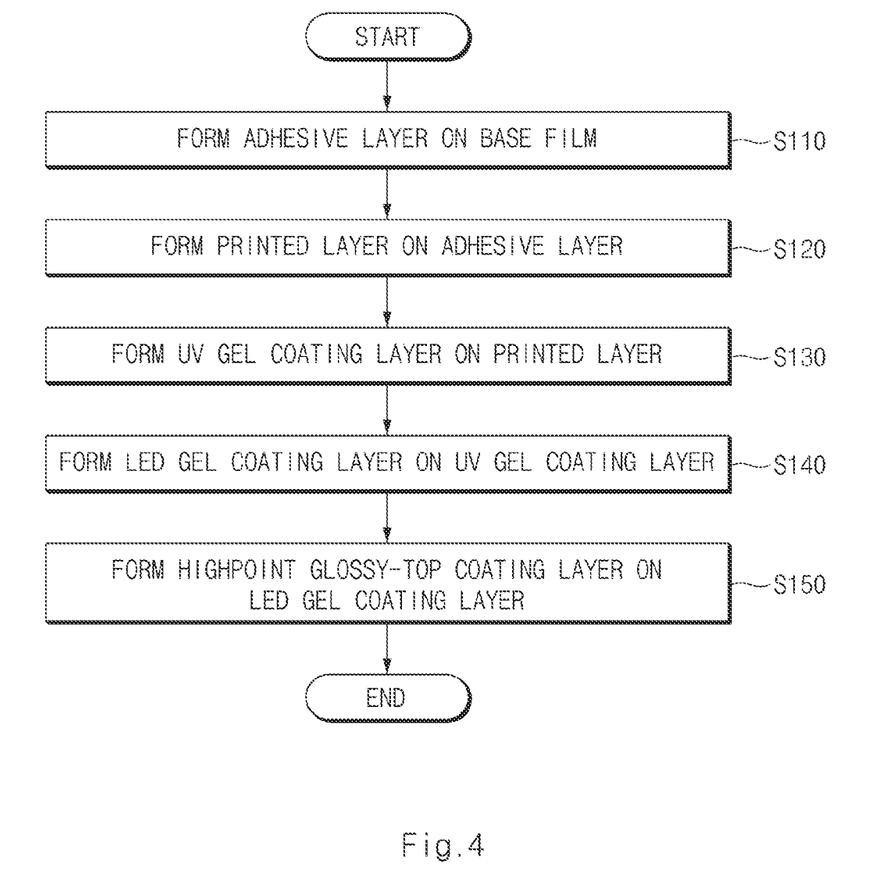
FIG. 4 is a flowchart illustrating a method of manufacturing an adhesive gel nail, according to an embodiment of the present disclosure.

FIG. 4 is a flowchart illustrating a method of manufacturing an adhesive gel nail, according to an embodiment of the present disclosure.

Referring to FIG. 4, an adhesive layer may be formed on a base film (S110). In this case, the base film may be a silicon release-treated fabric being a 125 micron PET film. Also, the adhesive layer may include an acrylic water-based adhesive and may include a nutritional enhancement component and an antibacterial component as an anti-fungal nutrient glue layer. For example, the nutritional enhancement component of the adhesive layer may include vitamin B5, vitamin E, calcium, and the like, and the antibacterial component thereof may include eucalyptus, cypress water, natural herbs, and the like.

A printed layer may be formed on the adhesive layer (S120). In this case, the printed layer may be formed by various printing manners such as silk screen printing, flexographic printing, offset printing, digital printing and gravure printing. Also, the printed layer may express a design through decorations such as gold leaf, silver leaf, hologram leaf, or glitter.

Meanwhile, although not illustrated in FIG. 4, the adhesive gel nail manufacturing method according to an embodiment of the present disclosure may further include forming an urethane sheet layer on the adhesive layer before the printed layer is formed. In this case, the urethane sheet layer may be formed by adding aerosol to an urethane raw material such that air holes are formed. This may allow the adhesive gel nail to have high oxygen permeability, that is, the adhesive gel nail may provide air permeability. Accordingly, when attaching the gel nail to his/her fingernails or toenails, the user may feel more comfortable, that is, may not feel stuffy.

Afterwards, an UV gel coating layer may be formed on the printed layer (S130). In this case, the UV gel coating layer may be formed by applying an UV gel coating solution, in which an oligomer, a monomer, and a short-wavelength initiator are mixed, and drying the UV gel coating solution in an ultraviolet curing manner. In this case, the oligomer may use urethane, acryl, acrylic epoxy, polyester-based oligomer, or the like, and the short-wavelength initiator may use TPO, 184, or the like. In addition, the applied UV gel coating solution may be dried in an UV curing manner to form the UV gel coating layer 50.

Afterwards, an LED gel coating layer may be formed on the UV gel coating layer (S140). In this case, the LED gel coating layer may be formed by applying and drying an LED gel coating solution in which an oligomer, a monomer, a long-wavelength initiator, and a cellulose are mixed. Also, the applied LED gel coating solution may form the LED gel coating layer 60 by drying the solution at a temperature of 60 to 100 degrees for 30 to 60 minutes.

Afterwards, a highpoint glossy-top coating layer may be formed on the LED gel coating layer (S150). In this case, the highpoint glossy-top coating layer 70 may be formed by applying and drying a glossy-top coating solution in which a monomer, an oligomer, a cellulose, and a long-wavelength initiator are mixed. In an embodiment, the highpoint glossy-top coating layer may have a shape in which a central portion thereof protrudes and may be harder than the LED gel coating layer formed in S140.

As described above, an adhesive gel nail according to an embodiment of the present disclosure may include nutritional and antibacterial components to prevent fingernails and toenails from being damaged. Also, the adhesive gel nail according to an embodiment of the present disclosure may provide a volume to the user's fingernails and toenails through a highpoint glossy-top coating layer. In addition, as air holes are formed within the adhesive gel nail such that oxygen permeability is improved, the adhesive gel nail may provide air permeability.

By an adhesive gel nail and a manufacturing method thereof according to an embodiment of the present disclosure, nutritional and antibacterial components may be included in the adhesive gel nail to prevent fingernails and toenails from being damaged.

By the adhesive gel nail and the manufacturing method thereof according to an embodiment of the present disclosure, the volume of the fingernails and toenails of the user may be implemented through a highpoint glossy-top coating layer.

By the adhesive gel nail and the manufacturing method thereof according to an embodiment of the present disclosure, air holes may be formed within the adhesive gel nail such that oxygen permeability is improved, and thus, the adhesive gel nail may provide air permeability.

In the above, even though all components constituting an embodiment of the present disclosure are described as being combined to one or operating in combination, the present disclosure is not necessarily limited to the embodiment. That is, within the scope of the invention, a part of all components may be selectively combined and may perform a function(s).

In addition, the terms such as "comprise", "include", and "have" described above mean that the corresponding component may be included, unless there is a particularly contrary statement, and should be interpreted as further including another component, not excluding another component. Unless otherwise defined herein, all the terms used herein, which include technical or scientific terms, may have the same meaning that is generally understood by a person skilled in the art. Terms commonly used, such as those defined in the dictionary, should be interpreted as having a meaning that is consistent with the meaning in the context of the related art and will not be interpreted as having an idealized or overly formal meaning unless expressly defined herein.

The above description is merely an example of the technical idea of the present disclosure, and various modifications and modifications may be made by one skilled in the art without departing from the essential characteristic of the invention. Accordingly, embodiments of the present disclosure are intended not to limit but to explain the technical idea of the present disclosure, and the scope and spirit of the invention is not limited by the above embodiments. The scope and spirit of the invention should be construed by the attached claims, and all equivalents thereof should be construed as being included within the scope of the invention.

What is claimed is:

1. An adhesive gel nail comprising:
    a base film;
    an adhesive layer on the base film;
    a printed layer on the adhesive layer;
    an UV gel coating layer on the printed layer;
    an LED gel coating layer on the UV gel coating layer; and
    a highpoint glossy-top coating layer on the LED gel coating layer,
        wherein the highpoint glossy-top coating layer is formed by applying and drying a glossy-top coating solution on the LED gel coating layer to provide a coating that forms a pointed peak shape, wherein the glossy-top coating solution is formed by:
            mixing 3% to 12% of a monomer, 9% to 25% of an oligomer, 60% to 88% of a cellulose, and 0.2% to 0.7% of a long-wavelength initiator at a temperature of 60° C. to 100° C. for 30 to 60 minutes.

2. The adhesive gel nail of claim 1, further comprising:
    an urethane sheet layer on the adhesive layer, wherein the urethane sheet layer is formed by adding aerosol to an urethane raw material such that air holes are formed.

3. The adhesive gel nail of claim 1, wherein the highpoint glossy-top coating layer has a shape in which a central portion thereof protrudes.

4. The adhesive gel nail of claim 1, wherein the highpoint glossy-top coating layer is harder than the LED gel coating layer.

5. The adhesive gel nail of claim 1, further comprising:
a protective film layer on the highpoint glossy-top coating layer,
wherein the protective film layer is capable of being cut without a cut line.

6. The adhesive gel nail of claim 1, wherein the adhesive layer includes a nutritional enhancement component and an antibacterial component.

7. The adhesive gel nail of claim 6, wherein the nutritional enhancement component includes vitamin B5, vitamin E, and calcium, and the antibacterial component includes eucalyptus, cypress water, and natural herb.

8. The adhesive gel nail of claim 1, wherein the adhesive gel nail has a modulus value of 1 Mpa to 35 Mpa.

9. The adhesive gel nail of claim 1, wherein the adhesive gel nail is 200 microns to 500 microns in thickness.

10. The adhesive gel nail of claim 1, wherein the adhesive layer includes an acrylic water-based adhesive.

11. The adhesive gel nail of claim 1, wherein the UV gel coating layer is formed by applying an UV gel coating solution, in which an oligomer, a monomer, and a short-wavelength initiator are mixed, and drying the UV gel coating solution via exposure to ultraviolet light.

12. The adhesive gel nail of claim 1, wherein the LED gel coating layer is formed by applying and drying an LED gel coating solution in which an oligomer, a monomer, a long-wavelength initiator, and a cellulose are mixed.

13. The adhesive gel nail of claim 1, wherein the printed layer is formed by at least one of silk screen printing, flexographic printing, offset printing, digital printing, and gravure printing.

14. A method of manufacturing an adhesive gel nail, the method comprising:
forming an adhesive layer on a base film;
forming a printed layer on the adhesive layer;
forming an UV gel coating layer on the printed layer;
forming an LED gel coating layer on the UV gel coating layer; and
forming a highpoint glossy-top coating layer on the LED gel coating layer,
wherein the highpoint glossy-top coating layer is formed by applying and drying a glossy-top coating solution on the LED gel coating layer to provide a coating that forms a pointed peak shape, wherein the glossy-top coating solution is formed by: mixing 3% to 12% of a monomer, 9% to 25% of an oligomer, 60% to 88% of a cellulose, and 0.2% to 0.7% of a long-wavelength initiator at a temperature of 60° C. to 100° C. for 30 to 60 minutes.

* * * * *